(12) United States Patent
Gerstmar

(10) Patent No.: US 7,320,671 B2
(45) Date of Patent: *Jan. 22, 2008

(54) MODULAR CERVICAL SUPPORT AND REDEFINITION STRUCTURE

(76) Inventor: Gail L. Gerstmar, 12933 SW. Wilimington La., Tigard, OR (US) 97224-1794

( * ) Notice: Subject to any disclaimer, the term of this patent is extended or adjusted under 35 U.S.C. 154(b) by 452 days.

This patent is subject to a terminal disclaimer.

(21) Appl. No.: 10/434,712

(22) Filed: May 7, 2003

(65) Prior Publication Data
US 2003/0195444 A1 Oct. 16, 2003

Related U.S. Application Data

(63) Continuation-in-part of application No. 09/952,359, filed on Sep. 12, 2001, now Pat. No. 6,595,935.

(51) Int. Cl.
A61F 5/00 (2006.01)

(52) U.S. Cl. .................. 602/18; 128/DIG. 23

(58) Field of Classification Search .......... 602/17, 602/18; 128/DIG. 23
See application file for complete search history.

(56) References Cited

U.S. PATENT DOCUMENTS

| | | | |
|---|---|---|---|
| 673,872 A * | 5/1901 | Flinsch | |
| 1,246,271 A * | 11/1917 | Hurd | |
| 3,964,474 A * | 6/1976 | Fox | 128/DIG. 23 |
| D248,872 S | 8/1978 | Thomas | |
| D278,747 S | 5/1985 | Peach, Jr. | |
| 4,562,833 A * | 1/1986 | Pujals | 602/18 |
| 4,576,150 A | 3/1986 | Auracher | |
| 4,708,129 A * | 11/1987 | Pujals, Jr. | 602/18 |
| 4,854,306 A * | 8/1989 | Pujals, Jr. | 602/18 |
| 4,934,357 A | 6/1990 | Frantzich et al. | |
| D324,734 S | 3/1992 | Burgess | |
| 5,271,114 A | 12/1993 | Kjersem | |
| 5,275,581 A | 1/1994 | Bender | |
| D369,660 S | 5/1996 | Myoga | |
| 5,685,613 A | 11/1997 | Franzen, Jr. | |
| 5,722,939 A | 3/1998 | Hohlen | |
| 5,904,662 A | 5/1999 | Myoga | |
| 5,979,456 A | 11/1999 | Magovern | |
| 6,009,577 A | 1/2000 | Day | |
| D422,710 S | 4/2000 | Maynard | |
| 6,056,711 A | 5/2000 | Domanski et al. | |
| 6,071,255 A | 6/2000 | Calabrese | |
| 6,595,935 B2 * | 7/2003 | Gerstmar | 602/1 |

* cited by examiner

*Primary Examiner*—Michael A. Brown

(57) ABSTRACT

A cervical support and redefinition structure which includes (a) an elongate collar that is removeably wrapable about a user's neck, with this collar having a central cervical region which is employable adjacent the cervix during use of the support structure to redefine the outside spatial profile of the cervix, and (b) pillow structure which is detachably connectable through connective interface structure, and in various different positions and orientations relative to the outside of the central cervical region, to cooperate with the collar in the providing of cervical support.

7 Claims, 4 Drawing Sheets

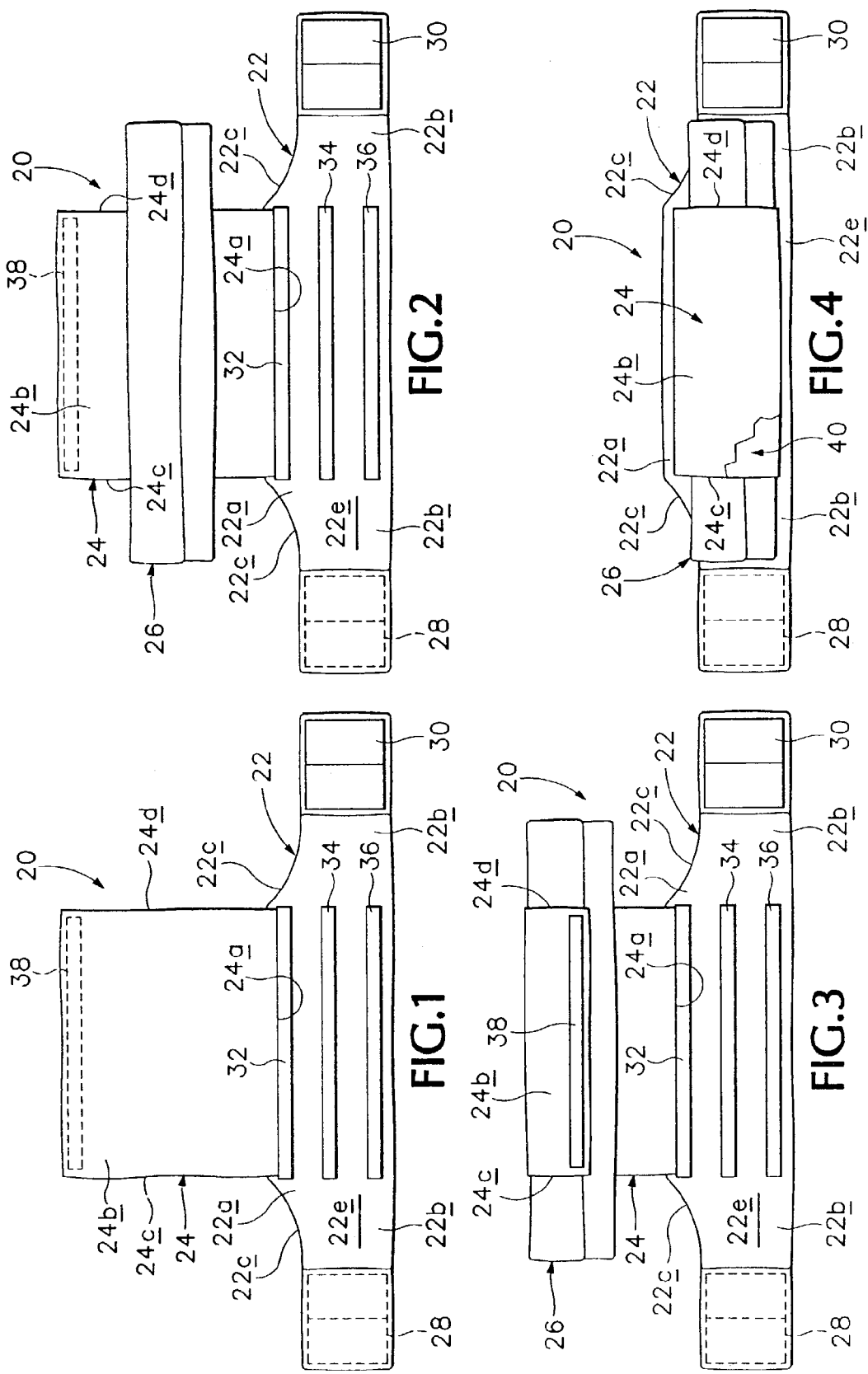

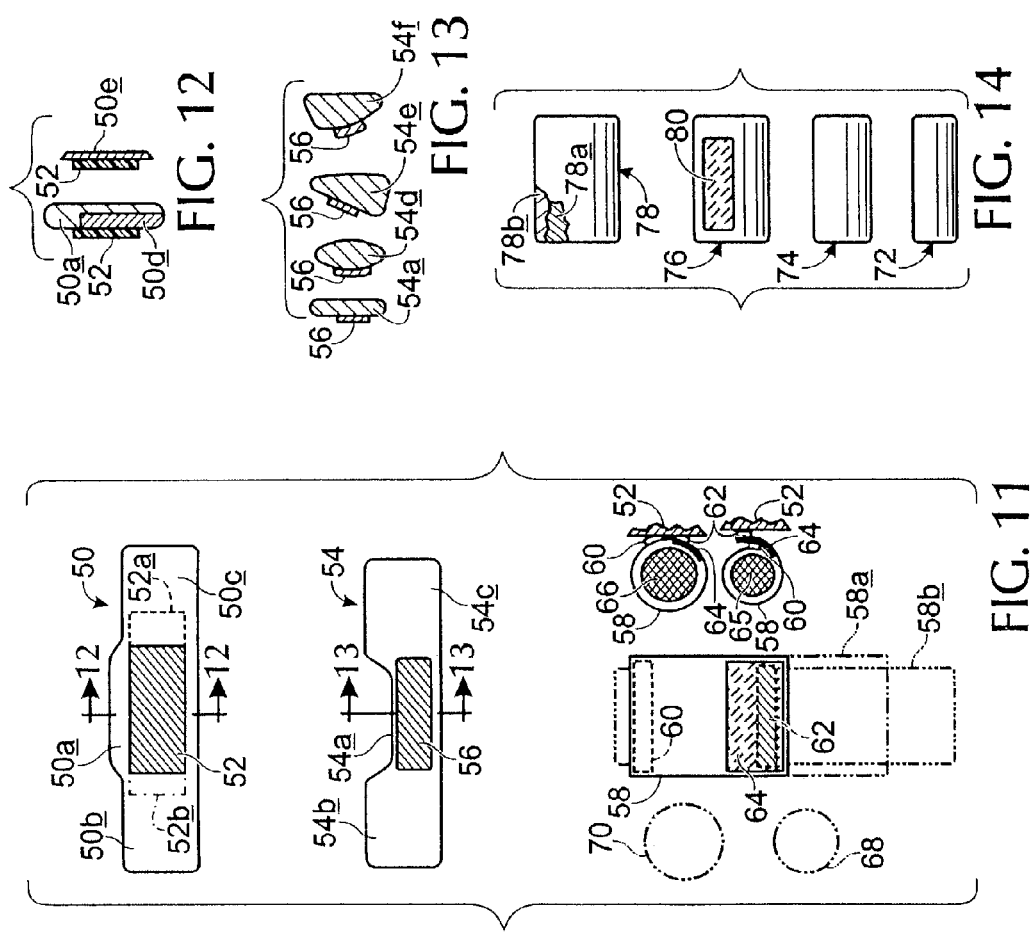

MODULAR CERVICAL SUPPORT AND REDEFINITION STRUCTURE

CROSS-REFERENCE TO RELATED APPLICATION

This application is a continuation-in-part of currently U.S. patent application, Ser. No. 09/952,359, filed Sep. 12, 2001, now U.S. Pat. No. 6,595,935 for "Cervical Support Structure". The entire contents of that prior application are hereby incorporated herein by reference.

BACKGROUND AND SUMMARY OF THE INVENTION

The present invention relates to modular cervical support and redefinition structure, and in particular, to such structure which features selectable, interactively cooperative components including an elongate cervical collar with a special, elongate, central, cervix-engaging, and spatial profile redefining cervical region which is adapted to receive, detachably, and either directly, or through an adjustable pillow-sling structure (also referred to both as a sling, and as a wrap), a pillow, or pillow structure.

There are many applications for cervical support structures. These typically take the form of an elongate cushioning collar that can be wrapped around a wearer's neck to engage, inter alia, the cervix, or a specially configured "free standing" pillow which is generally free from (i.e., not secured or attached to) a user, and which is employed with the user lying down with the back of the neck supported on the pillow. While both of these prior art cervical support devices have utility, the present invention recognizes a unique way, and furnishes a unique structure, for combining these dual utilities in highly reconfigurable manners, and in ways which enable effective, selective profile redefinition of the cervical area of the neck to enable specifically "tailored" cervical support.

In its fully operative condition with respect to a user, the collar of this invention is wrapped circumferentially, and removeably, about the user's neck, and an elongate, preferably, though not necessarily, cylindrical pillow is attached removeably to the back, central, cervical region of the collar, either directly, or through the mentioned adjustable sling structure. The sling structure, when used, forms an elongate, selectively sizeable, double-open-ended tube, also referred to herein as an adjustable receiving space, that receives and holds the pillow. This sling structure may be furnished in different, selectable sizes, with each such size being preferably chosen to handle, nominally, pillows (referred to as being modularity-characterized) having cross-sectional areas (trans-axial, cross-sectional configurations) that generally lie within a given size range.

Connective, interface attaching structure employed between the selected pillow and the central cervical region in the collar is designed, according to the invention, to enable easy and versatile, variable-disposition, removable attachment of the pillow in a wide variety of useful relative locations and orientations. The cross-sectional configuration of the collar's cervical region is modifiable, through collar selection, to function so as effectively to redefine the outside spatial profile of the cervix which, as so "redefined", can be uniquely and specially supported by a pillow to suit different cervical-support situations and conditions.

This combinational structure thus, while definitively offering a user substantially all of the advantages of the mentioned, individual, prior art cervical devices, provides, via unique modularity, and changeable relative positionability, of attachable/detachable components, many more features and advantages.

These and other features and advantages which are offered and attained by the present invention will become more fully apparent as the description which now follows is read in conjunction with the accompanying drawings.

DESCRIPTION OF THE DRAWINGS

FIGS. 1-4, inclusive, show different plan views of one form of the modular cervical support and redefinition structure of the present invention—a form in which a wrap, sling structure is permanently attached at one edge to the central cervical region of the collar component—illustrated in different stages of preparation for wearing and use by a user.

FIG. 11 presents a collection of views of various modular and inter-cooperative components, and certain specific modifications thereof, proposed in accordance with one preferred alternative aspect of the present invention.

FIGS. 12 and 13, taken generally as illustrated by lines 12-12 and 13-13 in FIG. 11, present several cross-sectional views of various modifications of central cervical regions in the cervical-collar components of the modular cervical support and redefinition structure (system) shown in FIG. 11.

FIG. 14 presents additional views of several component pillows, and specific modifications thereof, which are also illustrated in FIG. 11.

FIG. 15 is a stylized and schematic top plan view illustrating, by way of several moved-relative-position examples, how the modular components, and variations thereof, pictured in FIGS. 11-14, inclusive, may be assembled differently to address different cervical-support situations.

FIGS. 16-19, inclusive, illustrate several examples of cervical profile redefining as such is conveniently enabled by use of the present invention. Omitted in these four views, in order to focus upon the natures of several producible and representative cervical redefinitions, is the collar structure which is interposed the cervix and a pillow structure, and through which a pillow's cross-sectional configuration telegraphs to influence cervix profile

DETAILED DESCRIPTION OF THE INVENTION

Turning now to the drawings, and referring first of all to FIGS. 1-4, inclusive, indicated generally at 20 is one preferred embodiment of a cervical support and redefinition structure which is constructed in accordance with the present invention. Support structure 20 includes an elongate collar 22, a pillow sling structure, or wrap, 24, and one form of pillow, or pillow structure, shown at 26 in FIGS. 2, 3 and 4.

Collar 22 generally has the contoured configuration shown with a high-contour or wider central cervical region 22*a*, and a low-contour narrower pair of end regions 22*b*. Central cervical region 22*a* joins with regions 22*b* through concavely-curved regions 22*c*. As will be understood and illustrated, when the collar is in place wrapped around a user's neck, cervical region 22a resides above the shoulders and beneath the head, directly against the outside profile of the cervix.

Collar 22, as illustrated, is preferably formed of conventional materials including a cushioning foam core of any appropriate softness and/or firmness, with this core being covered by medical-grade stockinet material, such as seamless, cotton-knit tubing. The specific materials employed to make up collar 22 are not elements of the present invention, and thus are described herein in no further detail.

Figure 5:
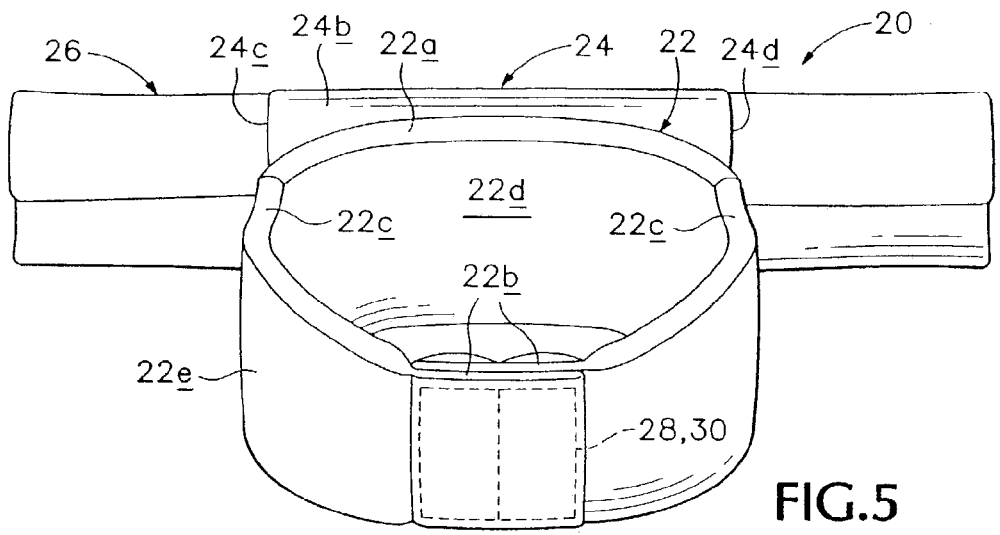
FIGS. 5 and 6 picture several different use conditions for the invention of FIGS. 1-4, inclusive.

Suitably secured as an attaching mechanism adjacent the outer ends of collar regions 22b are conventional, two-component, hook-and-loop fasteners, such as Velcro®, 28, 30, which accommodate removable securing of the collar to form an appropriate supportive circumferential structure about a user's neck, with central cervical region 22a disposed, as pointed out above, against the cervix. FIG. 5 illustrates (isolated from any user) such a circumferential configuration for collar 22. Such a two-component attaching mechanism will be referred to hereinafter, for convenience and clarity, as having A and B sides, or parts, which differ, and which interact to catch releasably with one another.

Suitably secured as an attaching mechanism adjacent the outer ends of collar regions 22b are conventional, two-component, hook-and-loop fasteners, such as Velcro®, 28, 30, which accommodate removable securing of the collar to form an appropriate supportive circumferential structure about a user's neck, with central cervical region 22a disposed, as pointed out above, against the cervix. FIG. 5 illustrates (isolated from any user) such a circumferential configuration for collar 22. Such a two-component attaching mechanism will be referred to hereinafter, for convenience and clarity, as having A and B sides, or parts, which differ, and which interact to catch releasably with one another.

Continuing now with reference to FIG. 5 along with FIGS. 1-4, inclusive, collar 22, with its central cervical region 22a, is seen to include an inside surface (inner side) 22d and an opposite, outside surface (outer side) 22e. As can be clearly seen, these inside and outside surfaces lie on opposite sides of region 22a, and face approximately in 180° opposite directions. Suitably attached centrally to outside surface 22e, within the lateral extent of elongate, central cervical region 22a, are elongate strips, or connector components, 32, 34, 36 which are alike in construction, and each of which takes the form of what can be thought of as one-half (such as a side A part) of a hook-and-loop, releasable attaching structure, like that previously mentioned. While three of these strips only are illustrated herein, it should be understood that a greater or lesser number could be employed. Also, the relative size proportions of these strips can differ according to the selected application for use of the structure of this invention. Further, a single appropriately sized (selectable) "patch" of this may be used if do desired. This structure, which is also referred to herein as modularity-configured, collar-resident attaching structure, forms a part of what constitutes a connective interface structure. Fastened (in the embodiment now being described herein) along one side of strip 32 is an edge 24a in a flexible, fabric-like flap 24b which makes up part of a pillow-sling structure, or wrap, 24. Attached to the upper free edge of flap 24b in FIGS. 1 and 2, and on the far side of the flap in these two figures, is another elongate fastener strip 38 which is designed to coact as a side-B interface connector part with any one of strips 32, 34, 36 in a hook-and-loop manner, effectively to close, or roll, the wrap upon itself, and to form an elongate, hollow receiving tube extending along the outside of cervical central region 22a of collar 22. Lateral edges 24c, 24d, the spaced side edges in flap 24b, form the edges of such a tube which is shown generally in FIG. 4 at 40. Such rolling of flap 24b to form a tube can be done in such a fashion as to form many different tubes with differing cross-sectional areas, depending upon to which one of strips 32, 34, 36, 38 become attached. Wrap 24 and strip 38 collectively form other parts of the just above-mentioned connective interface structure.

Pillow structure 26 herein takes the form of a rolled towel which, when rolled as generally shown in FIGS. 2-5, inclusive, forms an elongate cylindrical structure that is designed to be removeably received in a formed receiving tube of the type just previously discussed with respect to operation of pillow-sling structure 24. In FIG. 1, the pillow structure is absent. In FIG. 2, the pillow structure has been placed on the fully developed form of flap 24b, and in FIG. 3, curling or rolling of flap 24b is partially under way to create a receiving tube for the pillow structure. In FIG. 4, tube 40 is completely formed, and pillow structure 26 is seen to be confined within this tube, with the opposite ends of the cylindrical form of the pillow structure extending laterally outwardly as wings beyond the opposite ends of tube 40. Preferably, and as can be seen quite easily in FIGS. 4 and 5, with the pillow structure effectively connected to the collar, and disposed within tube 40, the pillow structure is essentially supported along much of its length within tube 40, whose supporting length generally matches the long dimension of central cervical region 22a in collar 22.

It should be evident that while a particular rolled, towel-like pillow structure is specifically disclosed in FIG. 5, such a pillow structure, which preferably, though not necessarily, has a cylindrical form, can be prepared in a number of different ways, and specifically can have different, selected, final, rolled or cylindrical diameters, depending upon the application and the user's wishes. It may also be a non-rolled structure, and one possessing different cross-sectional configurations. Thus, the structure of the invention contemplates allowing for significant size adaptability in this region, i.e., in the collar's cervical region, such adaptability being accommodated especially by the structure proposed for the pillow-sling structure and that proposed for the mentioned connective interface structure.

Looking now at FIGS. 1-10 collectively, in use, and with respect to the modular component structure so far described, a user prepares this structure to have generally the form pictured in FIG. 4. The user then wraps the collar circumferentially about his or her neck, and appropriately closes the opposite collar ends upon themselves to form a comfortable fit around the neck, such as is pictured in FIG. 8. In this condition, one will see that collar curved regions 22c lie generally along the jaw ridge-line area, and extend from slightly underneath the ears, and downwardly along and under the jaw, toward the space underneath the chin. The opposite ends of pillow structure 26 extend laterally beyond the closed collar as laterally extending wings, such as those that are clearly seen in FIG. 8. Central cervical collar region 22a resides directly against the spatial profile of the cervix.

Figure 8:
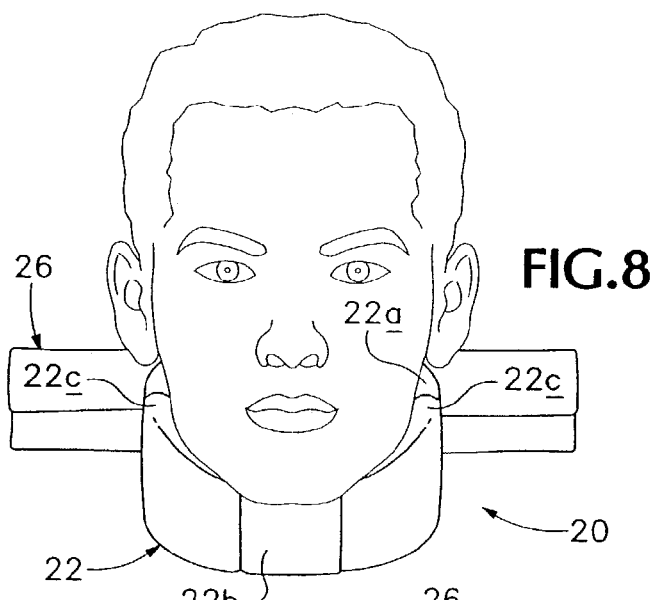
FIGS. 8-10, inclusive, picture the embodiment of the invention of FIGS. 1-4, inclusive, being worn by a user.
Figure 10:
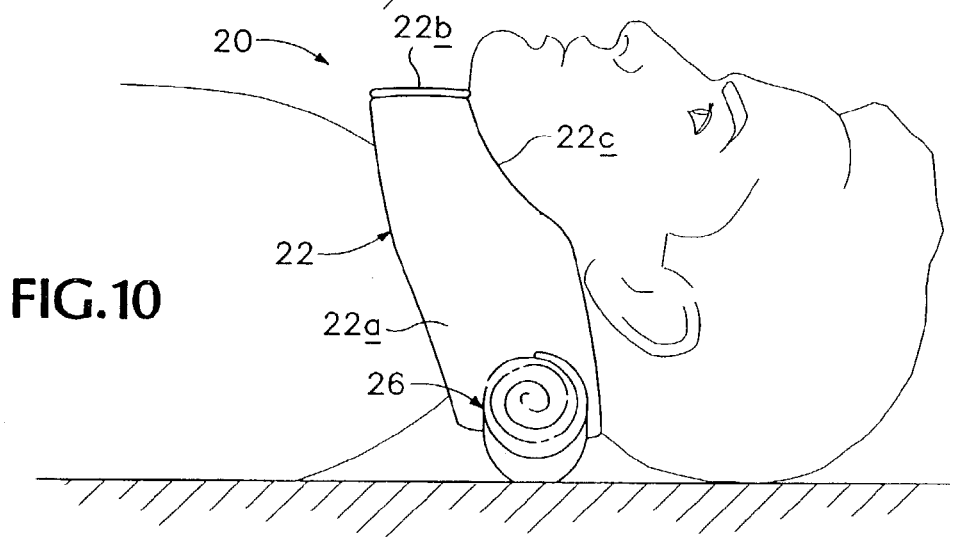

With the structure of this invention installed for use as pictured in FIG. 8, then, with the user's torso disposed generally upright, as in standing or sitting, or with the user simply lying on his or her back with the face looking straight up, the cervical region of the neck is given substantial support both by the collar structure, and by the pillow structure which works as a modularly cooperative attached unit with the collar structure in accordance with the invention. The portions of the collar structure which extend forwardly and beneath the chin stabilize the head. FIG. 10 illustrates a side view which is rotated clockwise relative to a view taken along the right side of FIG. 8, and shows this support condition.

Figure 6:
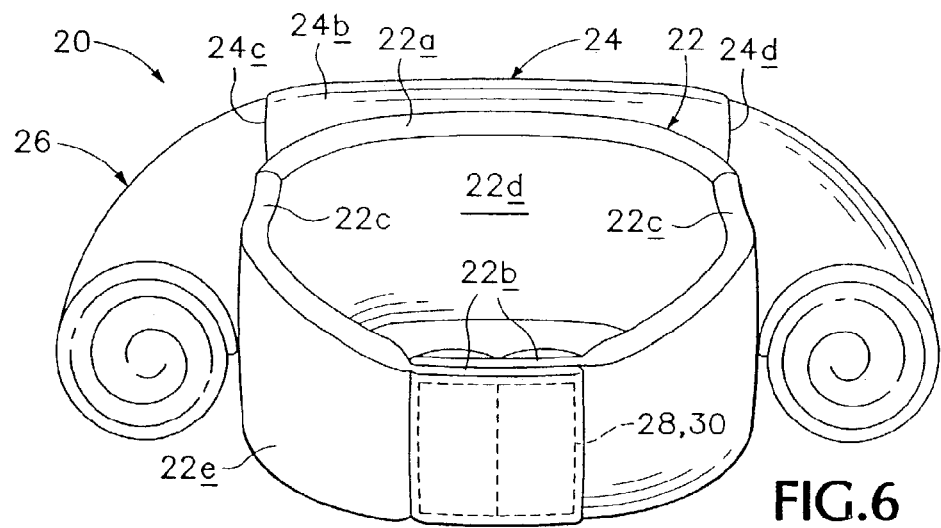
Figure 9:
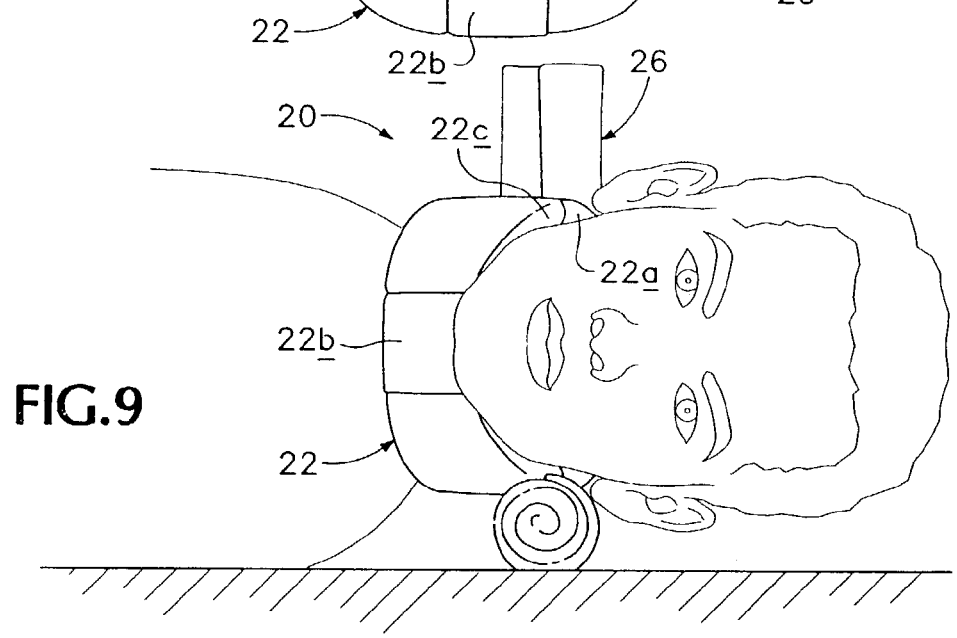

With the so far described device installed as thus shown, when the user is lying down, if he or she rolls the head and neck, or the whole body, toward one side, such as toward the viewer as shown in FIG. 9, the appropriate extending wing end of the pillow structure bends and curves to accommodate this positional adjustment, and does so specifically in a manner which continues to provide additional, combined collar and pillow support for what is now the side region of the wearer's neck adjacent the cervix. FIG. 6 in the drawings illustrates such a condition, with the extending ends of the pillow structure in this figure each being shown so bent and curved to indicate the bilateral accommodation capability of the structure of this invention.

Preferably, all modular components of the invention are made of materials which permit cleaning and repetitive multiple uses. As needed to suit different circumstances, and as will become more fully apparent from description herein shortly to follow, a user can vary the support characteristics of the device of this invention simply by varying the shapes and sizes of the pillow structure, as well as in other manners still to be discussed.

Figure 7:
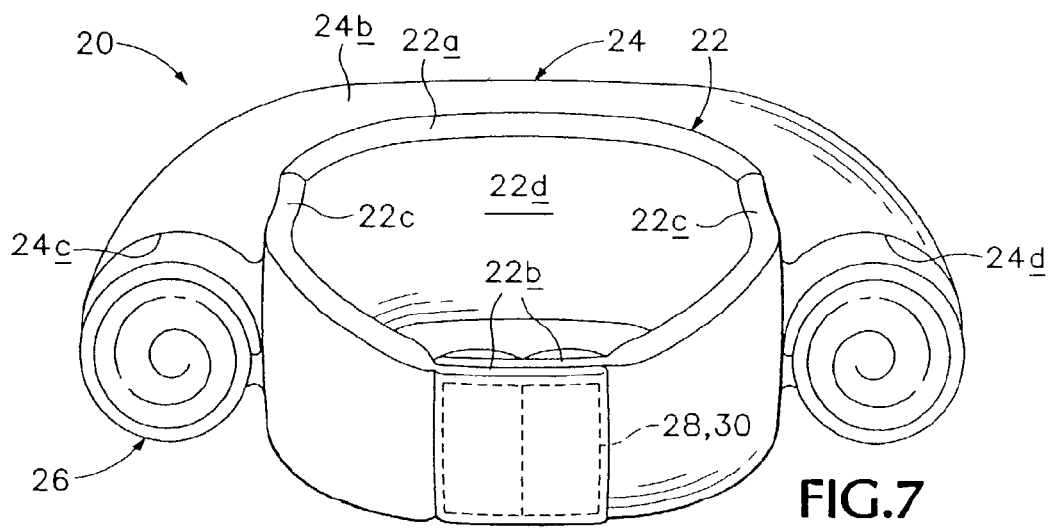
FIG. 7 shows a modified form of the general invention configuration shown in FIGS. 1-6, inclusive.

FIG. 7 in the drawings illustrates one useful modification wherein wrap 24 has been constructed with a significantly greater, overall lateral dimension so as to form, with the collar curved around a user's neck, an elongate curved tube adapted to receive an installed pillow structure. In this embodiment, a pillow structure is supported along a significantly greater length than that length of the support provided by the pillow-sling structure.

With attention now addressed to the remaining drawing figures, and turning first of all to FIGS. 11-14, inclusive, each of these figures presents a cluster of views illustrating certain modular components, and certain modifications thereof, made, in accordance with other preferred embodiments of the invention. Other illustrative modifications are simply described in text.

Illustrated at 50 in FIG. 11 is an elongate collar which is somewhat like previously mentioned collar 22. Collar 50 includes a central cervical region 50a, the opposite ends of which join with end regions 50b, 50c. The nominal cross-sectional configuration and appearance of central cervical region 50a is shown at the left side of FIG. 12, wherein it is pictured as having a slender and relatively tall upright appearance, with generally parallel and spaced inside and outside faces which are upright in FIG. 12. In FIG. 12, this appearance is highlighted by surface marking lines which slope downwardly and to the left.

Shown in solid outline in FIG. 12, and suitably and preferably permanently attached to the outside face of collar 50, the face which faces the viewer in FIG. 11, there is provided a singular elongate rectangular patch 52 of an appropriate attaching material which may preferably be "one side", such as the A side, of a conventional hook-and-pile fastener arrangement. Patch 52 forms part of what has been referred to herein previously as connective interface structure. Patch 52 extends laterally approximately to the opposite ends of central cervical region 50a, and also close to the upper and lower edges of this central cervical region. A dashed line 52a in FIG. 11 illustrates a modified patch which is off-center to the right in FIG. 11 relative to the center of region 50a, and which is somewhat longer than patch. A dash-dot line 52b in FIG. 11 illustrates another modified shape for a patch, like patch 52. Modified patch 52b is also somewhat longer than patch 52, and is disposed somewhat offset to the left of the central part of central region 50a.

One alternative form of the invention may feature a collar wherein, in any suitable manner, the specific material which is employed to form the outside (rear) surface, or face, of cervical region 50a is configured to be "one side" of a connective interface structure. Such a material may also simply be the covering material used entirely for the collar.

Looking for a moment particularly at FIG. 12, here, shown with two characters of cross-sectional shading which differ from that which is shown for central region 50a, and specifically at 50d and 50e, are two, modified cross-sectional configurations for central region 50a in collar 50. That which is shown at 50d has a smaller vertical dimension than that which characterizes region 50a as pictured, and also is somewhat thinner, i.e. more slender. Modified form 50e is even more slender, and possesses a vertical dimension which is somewhat between that shown for cross sections pictured at 50a, 50c. The inside and outside faces of these modified collar central-cervical regions (50d, 50e) are generally parallel to one another.

FIG. 12 thus shows certain modifications in the cross-sectional configuration of a central cervical region in a collar, like collar 50, and thus illustrates one feature of the present invention that involves selecting the cross-sectional configuration of this region, which, during use, will lie directly against the cervix as a step toward redefining the effective anatomical cervical area that will be directly engaged by a pillow in accordance with practice of this invention.

At 54 in FIG. 11, there is shown another elongate collar form made in accordance with yet another modified approach toward implementing this invention. Collar 54 includes a reduced-vertical-dimension central cervical region 54a having a cross section somewhat like that pictured at 50d in FIG. 12. This central cervical region in collar 54 joins with opposite end regions 54b, 54c. An A-type attaching patch 56, which is like previously mentioned patch 52, is joined to the outside surface, or face, of region 54a. As was also mentioned for previously discussed cervical region 50a, the outside, rear face of region 54a may be covered with an appropriate fabric material that can function as one side of an attaching interface connecting structure.

FIG. 13 illustrates several, different, modified transverse cross sections and configurations for central cervical region 54a. At the left side in FIG. 13, region 54a has a configuration very much like that which is shown at 50d in FIG. 12. At 54d, 54e, 54f in FIG. 13, three quite different illustrative cross sections are pictured. That shown at 54d is somewhat football shaped. That shown at 54e has a kind of rounded-corner triangular cross section, with the broad base of this cross section disposed at the lower side of the structure. The configuration shown at 54f is also a somewhat rounded-corner triangular configuration, with a broad triangular base located toward the upper part of the structure. Configurations 54d, 54e, and 54f are ones wherein the spaced inside and outside faces are not parallel with one another.

These additionally illustrated cross-sectional configurations for a central cervical region in a collar thus illustrate other selections which may be made to provide central cervical regions that coact with the spatial profile of a cervix during use of the invention. Specifically, these configurations furnish different kinds of profile redefinitions in accordance with the invention, thus to determine how an appropriately shaped and positioned, attached pillow will coact to provide user cervical support.

While not specifically illustrated in these figures which have just been discussed, the opposite ends of collars 50, 54 are appropriately provided with releasable closure structure that enables the collar to be attached and secured in a wrapped condition around a user's neck.

Toward the lower side of FIG. 11, various useful modifications of two other components in the modular structure of this invention, namely, a pillow-sling structure, or wrap, and various sizes and configurations of attachable pillows, are shown.

Illustrated at 58 in solid lines is a flexible, fabric-like, rectangular wrap having one selected set of longitudinal and lateral dimensions. In dash-double-dot lines in FIG. 11, a modified wrap 58*a* is shown which has substantially the same lateral dimension as does wrap 58, but a considerably larger longitudinal dimension. At 58*b* in FIG. 11, yet another differently configured wrap is illustrated which has still a larger longitudinal dimension, but in this case, a smaller lateral dimension.

Specifically illustrated as being secured to wrap 58 are three hook-and-pile connector patches 60, 62, 64. Patches 60, 62 are of like construction with respect to forming one operative "side", such as the B side, of a releasable hook-and-file attaching mechanism, and are secured to the far (not directly seen) face of wrap 58 in FIG. 11, near the upper and lower ends, respectively, of that wrap as pictured. Patch 64 is secured to the near face of wrap 58 in FIG. 11, and toward the bottom end of the wrap. This patch is formed of A-side hook-and-pile material.

According to the present invention, a wrap, such as wrap 58, is sized in length so as to be able nominally to accommodate and be wrapped around support pillows, or pillow structures, that lie within a certain defined range of cross-sectional configurations and sizes. In the sense of the word "nominal" now being employed, this is intended to indicate a situation wherein wrap 58 may be wound around the outside surface of a pillow, such as an elongate cylindrical pillow, so as to fit in close complementary adjacency, without necessarily squeezing upon and compressing a received pillow. One should also understand, however, that this very same wrap may be employed with respect to such a nominally receivable pillow in a manner which allows for intentional squeezing and compressing of the pillow, thus to change its effective cross-sectional configuration, if such a practice is desired in order to accomplish a particular kind of cervical-support behavior.

Shown at 65, 66 in FIG. 11, are two elongate cylindrical pillows which nominally have different cross-sectional diameters. These pillows are within the range of nominal sizes just mentioned with respect to the selected longitudinal dimension of wrap 58. Pillow 65 has a smaller diameter than does pillow 66.

Pillow 65 is shown encircled by wrap 58, with the wrap closing upon itself and fastening in a tube configuration about the pillow through interactive releasable attachment of fastener patches 60, 64. Patch 62, as can be seen, is exposed on the outside of this wrap-formed tube, and is shown releasably connected/attached to previously mentioned patch 52.

Larger pillow 66 is shown in FIG. 11 encircled by wrap 58 with, in this case, wrap 58 not completely closing on itself, but nevertheless forming a substantially completely encircling tube around the circumference of pillow 66. Here, wrap 58 assists in the interfacial connection which is established between the collar and pillow 66 through releasable attachment of patches 60, 62 with patch 52.

Shown at 68,70 in dash-double-dot lines in FIG. 11 are two more elongate, cylindrical pillows which are somewhat bigger in diameter than pillows 65, 66. More specifically, pillow 68 is slightly larger in cross-sectional diameter than is pillow 66, and pillow 70 is slightly larger in the same way with respect to pillow 68. These two pillows lie within a larger range (cross-sectional size range) of pillows with respect to which the somewhat longer wrap 58*a* is designed for use.

Turning attention now to FIG. 14, here there are shown four, elongate, cylindrical pillows, or pillow structures, 72, 74, 76, 78 which are roughly the same sizes, respectively, as previously discussed pillows 65, 66, 68, 70, respectively. Whereas pillows 65, 66, 68, 70 were discussed specifically in the context of being modular components constructed in accordance with the invention which are intended to be joined through an independent and separable wrap to the outside cervical region of a collar, pillows 72, 74, 76, 78 are illustrated herein as being equipped, in two different ways, for direct attachment to a collar, such as to collar 50 through an attaching patch 52. For the purpose of illustration herein, pillow 76, which is somewhat comparable in size to previously mentioned pillow 68, is equipped with a Velcro® patch 80 (B side) secured to it at a desired location. Patch 80 is designed to be detachably connectible to an attaching patch, such as patch 52 on collar 50.

Pillow 78 is designed somewhat differently, and very specifically is designed with a central core, or body, 78*a* which is jacketed by a covering 78*b* that is appropriately structured to be detachably attachable to a connective patch, such as patch 52.

Pillow 72, 74, with respect to which such details of construction are not specifically illustrated, should be understood to be constructible to have direct attaching capabilities like either one of those two capabilities illustrated for pillows 76, 78.

It should be understood, as mentioned earlier, that, while pillows have been described herein which have generally cylindrical configurations, with generally circular cross sections, pillows possessing other cross-sectional outlines may conveniently and effectively be employed if desired.

Turning attention now to FIG. 15, this figure shows schematically a plan view of the modular system, or structure, of the invention. This view utilizes collar 50 and pillow 72 for illustration purposes. In solid outline in FIG. 15, collar 50 is shown not completely closed upon itself, and pillow 72 is shown attached, in a center-to-center manner, to the rear, outer side of central cervical region 50*a* in collar 50 As is indicated by a collection of quite self-explanatory double-ended straight and curved arrows 82, 84, 86 in FIG. 15, a story is told which describes the capability of the modular structure of the present invention to allow for selective and infinitely variable, different relative positioning between pillow 72 and collar 50. Various dashed and dash-double-dot lines in FIG. 15 illustrate how pillow 72 may be shifted along its length to attach differently to the rear outer side of cervical region 50*a*. Certain ones of these lines also point out how the pillow structure may be angulated with respect to the central portion of region 50*a*. Obviously, what is shown in FIG. 15 represents variable positionability of a pillow with respect to a collar, with the long axis of such a pillow generally lying in a plane which parallels the plane of FIG. 15. It should be understood that angulation of a pillow and a collar in a direction generally normal to the plane of FIG. 15 is also entirely possible, if so desired.

Referring now to FIGS. 16-19, inclusive, these figures further illustrate the important and interesting capability of the present invention to effect a redefinition of the spatial profile, seen as a lateral profile schematically in these four figures, of the cervix region of the neck. The outwardly facing cervical profile per se is illustrated in a stylized, deeply curved schematic way by a solid curved line 90 in these four figures. The term "per se" here means the normal, or un-redefined cervical profile. Stylized dash-dot lines on the right sides of these four figures illustrate redefined cervical profiles as effected by engagements with four different illustrative cross sections for the cervical region of a collar.

Utilizing, as illustrations, several of the differentiated cross-sectional configurations pictured in FIGS. 12 and 13 for a cervical region of a collar in accordance with this invention, FIGS. 16-19, inclusive, clearly illustrate how, through selection of a particular cross-sectional configuration for such a region, the modular support structure of the present invention can readily redefine the cervical profile. Specifically, it can redefine this profile in a manner whereby a pillow which is employed will specifically engage remaining exposed regions of the cervix, and adjacent anatomical structure, in ways that allow for different selectable kinds of cervical support to take place. In FIG. 16, a cervical-region cross-sectional configuration like that shown at 50e in FIG. 12 is employed. This configuration very modestly and slightly redefines the effective cervical profile, such redefinition being pictured by a dash-dot line in FIG. 16. In FIG. 17 a cervical region profile somewhat like that pictured at 54e in FIG. 13 is employed, and here, a redefined cervical profile is also indicated by a dash-dot line. FIGS. 18 and 19 illustrate other cervical-profile redefinitions which are created utilizing cervical region collar profiles somewhat like those shown at 54f and 54d, respectively, in FIG. 13.

With regard such spatial redefining of the cervical profile, by appropriately selecting a particular cross-sectional configuration for the collar's central cervical region, and by selecting, for example, the cushioning qualities and cross-sectional configuration of an attachable pillow, cervical-profile re-defining which is dictated by the collar's cervical region can create a unique and tailored condition of cervical support. In this tailored condition, just where and how an attached pillow offers cervical support independently of its through-collar support, i.e., as by directly contacting the anatomy above and/or below the region occupied by the collar's central cervical region, becomes a definable and controllable matter.

In all current circumstances, and as can be seen especially clearly in FIGS. 8-10, inclusive, and in FIGS. 16-19, inclusive, when the structure of this invention is worn by a user, there exists a line-of-action, so-to-speak, which extends through and from an attached pillow, thence through the earlier mentioned inside and outside surfaces of the cervical region of the collar, and thence through the users's cervix and neck. This line-of-action results from the observable fact that, when the structure of this invention is in place on a user, the attached pillow effectively lies on the opposite side (the outer side) of the central cervical region of the collar relative that side (the inner side) which contacts the cervix. With such a line-of-action in place, support forces directed toward the neck through an attached pillow cause the pillow to "drive" the collar's cervical region against the user's cervix.

Thus, the modular support and cervical redefinition structure of this invention clearly offers not only all of the expected and customary advantages of conventional cervical support structures, but in addition, and through uniting a specially designed collar and a cooperative pillow through various different kinds of interfacial connective structure, offers, considerably more and versatile opportunities for providing cervical support.

It should be clear, from the description that has been given herein of the present invention, that various dimensions can easily be selected to suit a wide range of different applications (i.e., head sizes, neck sizes, etc.).

Accordingly, while various forms of the invention, have been illustrated and described herein, it is understood that other variations and modifications may be made without departing from the spirit of the invention.

I claim:

1. Modular cervical support and redefinition structure comprising
    a collar having a central cervical region, and possessing opposite-side inside and outside surfaces and upper and lower edges, removeably wrapable about a user's neck with said inside surface disposed directly adjacent the neck, said central cervical region disposed against the cervix, and said outside surface facing substantially 180° rearwardly away from the neck, and
    pillow structure removeably attachable to said outside surface of said collar at the location of said central cervical region, and substantially vertically centrally between said upper and lower edges, to coact with the collar, outwardly and rearwardly thereof, in the furnishing of cervical support for the user with such coaction taking place along a line-of-action which extends from the pillow structure, through said collar's opposite-side inside and outside surfaces, and through the central cervical region of the collar to the user's cervix, and with this line-of-action lying in a plane which, with said support and redefinition structure in use by a user, intersects said collar, said pillow structure, and the user's neck and cervix, at a location which is generally vertically centered on the user's cervix.

2. The structure of claim 1 which further includes adjustable pillow-sling structure operable on said outside surface of said collar in cooperation with said pillow structure to form an adjustable-receiving-space wrap adjacent the collar for containing said pillow structure, and for assisting in removeably attaching the pillow structure to the collar.

3. Modular, selectively configurable, cervical region-defining and support structure comprising
    an elongate cervical collar wrapable in a circumsurrounding fashion around the neck, and including an elongate, central cervical region having an inside surface which is disposed against the cervix during use of the structure, an opposite-side outside surface facing substantially 180° rearwardly away from the neck, and upper and lower edges, said cervical region having a transverse cross section which is selectively shaped relative to the spatial outer-surface profile of the cervix to furnish, via spatial collaboration between said cervical region's opposite-side outside surface and the cervix' outer-surface profile, a selected, effective outside-redefinition of that profile,
    modularity-configured collar-resident attaching structure joined to said cervical region's said opposite-side outside surface substantially vertically centrally between said edges,
    elongate, modularity-characterized pillow structure having a trans-axial cross-sectional configuration selectable to coordinate in a defined manner with such an effectively redefined cervical profile to furnish predetermined-characteristic cervical support along a line-of-action which extends from the pillow structure, and through the central cervical region of the collar to the user's cervix, and with this line-of-action lying in a plane which, with said region-defining and support structure in use by a user, intersects said collar, said pillow structure, and the user's neck and cervix, at a location which is generally vertically centered on the user's cervix, and connective interface structure operatively interposable said collar-resident attaching structure and said pillow structure on said cervical region's said opposite-side outside surface enabling selective, infinitely configurable, detachable attachment between the pillow structure and the collar-resident attaching structure.

4. A modular cervical support and redefinition structure comprising a collar having a central cervical region, and opposite-side inside and outside surfaces, and upper and lower edges, removeably wrapable about a user's neck with said inside surface directly adjacent the neck, said central cervical region disposed against the cervix, and said outside surface facing rearwardly away from the neck, pillow structure removeably attachable to the outside surface of said collar at the location of said central cervical region, and substantially vertically centrally between said edges, to coact with the collar, outwardly thereof, in the furnishing of cervical support for a user along a line-of-action which extends from the pillow structure, through said opposite-side inside and outside surfaces, and through the central cervical region of the collar to the user's cervix, and with this line-of-action lying in a plane which, with said support and redefinition structure in use by a user, intersects said collar, said pillow structure, and the user's neck and cervix, at a location which is generally vertically centered on the user's cervix, and connective interface structure operatively interposable said collar's central cervical region and said pillow structure on said cervical region's said opposite-side outside surface accommodating removable, variable-disposition attachment of the pillow structure to the collar's cervical region at a location which is substantially vertically central relative to said upper and lower edges.

5. The structure of claim 4, wherein said cervical region is elongate, and possesses a transverse cross-sectional configuration which is selected from the group including (a) inner and outer sides generally parallel to one another, and (b) inner and outer sides non-parallel to one another.

6. The structure of claim 4, wherein said connective interface structure includes a pair of connector components, one mounted on the collar's central cervical region, and one mounted on the pillow structure, enabling substantially direct interconnection between the central cervical region and the pillow structure.

7. A modular cervical support and redefinition structure comprising a collar having a central cervical region, and inside and outside surfaces, removeably wrapable about a user's neck with said inside surface directly adjacent the neck, and said central cervical region disposed against the cervix, pillow structure removeably attachable to the outside surface of said collar at the location of said central cervical region to coact with the same, outwardly thereof, in the furnishing of cervical support for a user along a line-of-action which extends from the pillow structure, and through the central cervical region of the collar to the user's cervix, and connective interface structure interposable said collar's central cervical region and said pillow structure, accommodating removable, variable-disposition attachment of the pillow structure to the collar's cervical region, said interface structure including a flexible wrap which is adapted to receive and hold a pillow and which is detachably attachable to said central cervical region on the outside surface thereof.

* * * * *